United States Patent [19]

Zimmerman

[11]  4,278,797
[45]  Jul. 14, 1981

[54] INTERMEDIATES TO PHENYLMORPHANS AND METHOD OF PREPARATION THEREOF

[75] Inventor: Dennis M. Zimmerman, Mooresville, Ind.

[73] Assignee: Eli Lilly and Company, Indianapolis, Ind.

[21] Appl. No.: 150,763

[22] Filed: May 19, 1980

Related U.S. Application Data

[62] Division of Ser. No. 19,527, Mar. 12, 1979, abandoned.

[51] Int. Cl.$^3$ ............................................. C07D 221/22
[52] U.S. Cl. ...................................... 546/112; 546/339; 546/344; 546/350; 424/267
[58] Field of Search ........................................... 546/112

[56] References Cited

U.S. PATENT DOCUMENTS 3,951,984   4/1976   Kimura et al. ................... 546/112 X
4,079,141   3/1978   Ong et al. ........................ 546/112 X

FOREIGN PATENT DOCUMENTS 5041869   4/1975   Japan ...................................... 546/112

OTHER PUBLICATIONS

May, E. et al., *J. Org. Chem.*, 20, 1197, (1955).
Rogers, M., et al., *J. Med. Chem.*, 17, 1328, (1974).
Takeda, M., et al., *J. Med. Chem.*, 20, 221, (1977).

*Primary Examiner*—Richard A. Schwartz
*Attorney, Agent, or Firm*—Charles W. Ashbrook; Arthur R. Whale

[57] ABSTRACT

Phenylmorphans having substituents at the 2, 3 and 7 positions and intermediates thereof are disclosed. The compounds exhibit potent analgesic activity. Formulations and a method of relieving pain are provided.

17 Claims, No Drawings

INTERMEDIATES TO PHENYLMORPHANS AND METHOD OF PREPARATION THEREOF

This is a division, of application Ser. No. 19,527, filed Mar. 12, 1979, now abandoned.

BACKGROUND OF THE INVENTION

Analgesics are widely used in the treatment of mild pain due to CNS disorders and of more severe pain due to diseases such as cancer. Many of the agents commonly used to relieve instances of severe pain are extremely dangerous due to their potency and to their addicting properties. Morphine is among such analgesic agents, and causes severe physical dependence. Even with such drawback, morphine is extensively used simply because of the non-existence of a more desirable agent. A great deal of research has been devoted, however, to finding compounds capable of alleviating severe pain to the degree accomplished with morphine, but which display little or no physical dependence capacity. Among the more recent discoveries is the series of compounds referred to generally as the "phenylmorphans." May and Murphy reported that racemic 5-(3-hydroxyphenyl)-2-methylmorphan possesses an analgesic potency nearly equivalent to that of morphine, J. Org. Chem., 20, 1197 (1955). May and Takeda later reported that the (−)-isomer of 5-(3-hydroxyphenyl)-2-methylmorphan is an analgesic with morphine-like potency but with no physical dependence capacity, J. Med. Chem., 13, 805 (1970).

One of the major difficulties with the early syntheses of this extremely potent series of compounds was the low overall yields and the difficulty in handling the intermediates. Rogers and May recently reported an improved synthesis of (−)-5-(3-hydroxyphenyl)-2-methylmorphan, but still the overall yield was only one percent, J. Med. Chem., 17, 1328 (1974). A number of novel 5-(3-hydroxyphenyl)-2-(substituted)morphans have been prepared and evaluated by Ong and co-workers, J. Med. Chem., 17, 133 (1974). None, however, were as potent as the 5-(3-hydroxyphenyl)-2-methylmorphan.

To date, no phenylmorphans having various substituents at positions other than the morphan 2-position have been prepared. An object of this invention is to provide certain 5-phenylmorphans having alkyl and alkenyl substituents at the 3 and 7-positions. Another object of the invention is to provide an improved synthesis of both new and known phenylmorphans.

SUMMARY OF THE DISCLOSURE

This invention relates to 5-phenylmorphans and to a process for their preparation. The invention more particularly provides phenylmorphan analgesics defined by the general formula

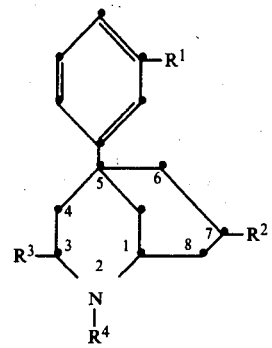

wherein:

$R^1$ is hydrogen, hydroxy or $C_1$-$C_3$ alkoxy;

$R^2$ and $R^3$ independently are hydrogen, $C_1$-$C_5$ alkyl or $CH_2C_2$-$C_4$ alkenyl, provided that $R^2$ and $R^3$ both are not hydrogen;

$R^4$ is $C_1$-$C_{10}$ alkyl, $C_1$-$C_3$ alkylphenyl, $CH_2C_2$-$C_9$ alkenyl, $CH_2C_3$-$C_6$ cycloalkyl; and the pharmaceutically acceptable acid addition salts thereof.

Preferred compounds of the invention are those wherein $R^1$ is hydrogen, hydroxy or methoxy; $R^2$ and $R^3$ independently are hydrogen or n-$C_1$-$C_5$ alkyl; and $R^4$ is n-$C_1$-$C_{10}$ alkyl, benzyl, 2-phenethyl, $CH_2C_2$-$C_3$ alkenyl and $CH_2C_3$-$C_4$ cycloalkyl.

Also contemplated by this invention are pharmaceutical formulations useful in the treatment of pain comprising an analgesically effective amount of a phenylmorphan defined by the above formula in combination with a suitable pharmaceutical carrier or excipient therefor. Additionally provided is a method of imparting analgesia in animals comprising administering to a subject suffering from pain and in need of treatment an analgesically effective dose of a phenylmorphan defined by the above general formula.

An important intermediate in the synthesis of compounds having the above formula is a compound defined by the formula

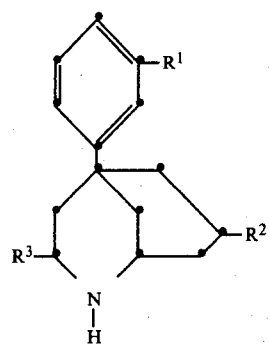

wherein $R^1$, $R^2$ and $R^3$ are as defined above.

Additionally provided by this invention are dehydrophenylmorphan intermediates of the formulas

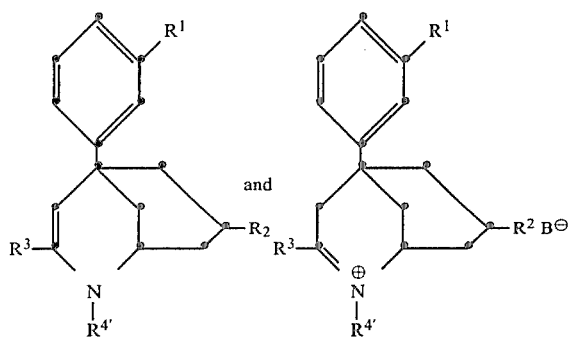

wherein:

R¹ is hydrogen, hydroxy or $C_1-C_3$ alkoxy;

R² is hydrogen, $C_1-C_5$ alkyl or $CH_2C_2-C_4$ alkenyl;

$R^{4'}$ is a subgroup of the above-defined $R^4$ and is selected from $C_1-C_{10}$ alkyl, $C_1-C_3$ alkylphenyl or $CH_2C_3-C_6$ cycloalkyl; and $B^\ominus$ is an anion of a protonic acid.

The dehydrophenylmorphan compounds defined by the above formulas are useful in the preparation of known 5-phenylmorphans as well as the new 5-phenylmorphan analgesics of this invention. The 2,3-dehydrophenylmorphanium salts are prepared by a novel process which also is provided by this invention and comprises reacting a tetrahydropyridine having the formula

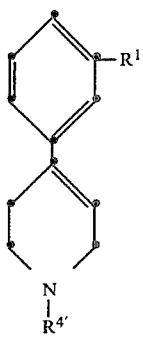

with a propenyl alkylating agent of the formula

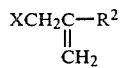

$$XCH_2C-R^2$$
$$\overset{\|}{CH_2}$$

wherein R¹, R² and $R^{4'}$ have the above-defined meanings, and X is a good leaving group, in the presence of a strong base to provide a 1,4,5,6-tetrahydro-4-phenylpyridine of the formula

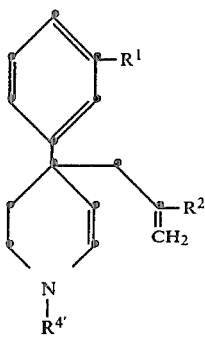

and reacting said compound with a protonic acid of the formula HB, in which B is an anion.

DETAILED DESCRIPTION OF THE INVENTION

As used throughout this specification and in the appended claims, R¹ includes "$C_1-C_3$ alkoxy" such as methoxy, ethoxy and n-propoxy. A preferred alkoxy group is methoxy.

R² and R³ are defined to include "$C_1-C_5$ alkyl" groups such as methyl, ethyl, n-propyl, isopropyl, n-butyl, n-pentyl and isopentyl, as well as "$CH_2C_2-C_4$ alkenyl" groups such as allyl, 3-butenyl, 2-pentenyl, 2-methyl-2-butenyl and the like.

R⁴ as defined herein includes "$C_1-C_{10}$ alkyl" groups such as methyl, ethyl, n-pentyl, isohexyl, 2-methylheptyl, 1,1-dimethylheptyl, 2-ethyloctyl, n-nonyl, n-decyl, and related alkyl groups. R⁴ also includes "$C_1-C_3$ alkylphenyl" groups such as benzyl, 2-phenethyl and 3-phenylpropyl. The term "$CH_2C_2-C_9$ alkenyl" refers to groups such as allyl, 3-butenyl, 3-pentenyl, 4-hexenyl, 2,3-dimethyl-2-pentenyl, 3-octenyl, 5-decenyl and the like. R⁴ additionally includes "$CH_2C_3-C_6$ cycloalkyl" groups such as cyclopropylmethyl, cyclobutylmethyl, cyclopentylmethyl and cyclohexylmethyl. Cyclopropylmethyl is a preferred cycloalkyl substituent.

The phenylmorphan compounds provided by this invention are prepared by reacting a 1-alkyl-4-phenyl-1,2,5,6-tetrahydropyridine with a strong base such as butyl lithium or phenyl lithium and a propenyl alkylating agent such as allyl bromide to provide a 1-alkyl-4-phenyl-4-(2-propenyl)-1,4,5,6-tetrahydropyridine. The latter compound is reacted with a protonic acid to effect ring closure with concomitant double bond migration to give a 2-alkyl-2,3-dehydro-5-phenylmorphanium salt. Reduction of the double bond of such salt affords the corresponding 3-unsubstituted phenylmorphan, whereas alkylation of the 2,3-dehydro-5-phenylmorphanium salt provides the corresponding 3-substituted-phenylmorphan of the invention. The overall reaction is depicted in the following general scheme:

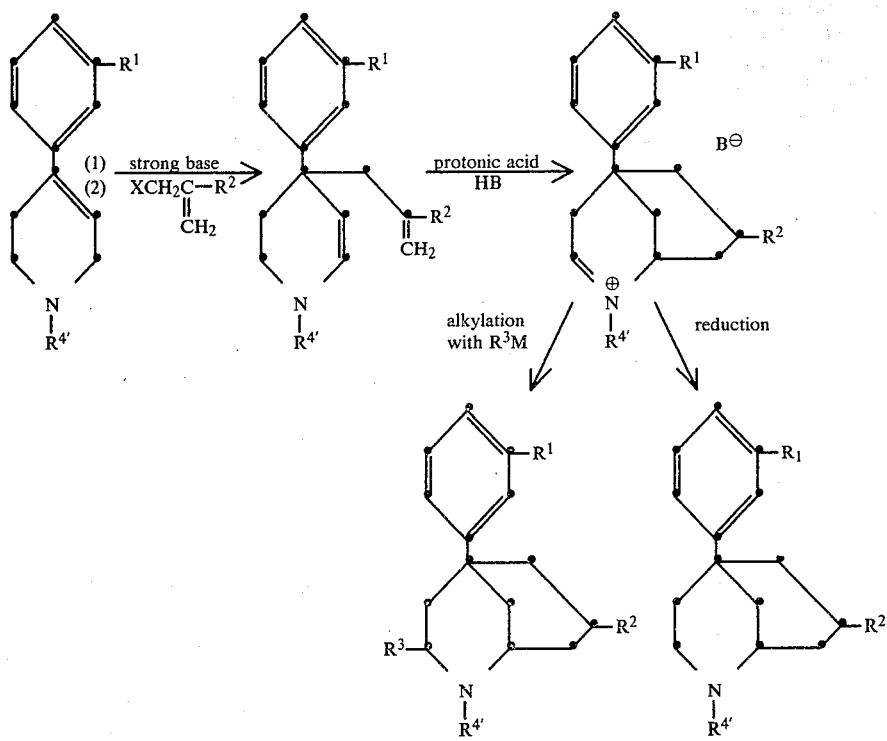

In the above scheme, $R^1$, $R^2$, $R^3$ and $R^{4'}$ are as defined hereinbefore, X is a leaving group and B and M are ionic radicals. It should be noted that when the above reactions are carried out wherein $R^1$ is methoxy, $R^2$ and $R^3$ both are hydrogen and $R^{4'}$ is methyl, the compound prepared is one disclosed by Rogers et al. in *J. Med. Chem.* 17, 1328 (1974), and is a precursor to the potent analgesic 2-methyl-5-(3-hydroxyphenyl)morphan. The process provided herein is an improvement over the prior art processes for preparing phenylmorphans since the product is produced in over fifty percent yield whereas the prior art processes produce the product in less than ten percent overall yield.

The first step in the process of this invention is the reaction of a 4-phenyl-1,2,5,6-tetrahydropyridine with a strong base and a propenyl alkylating agent. Strong bases commonly utilized in the reaction include lower alkyl metalides such as methyl lithium, methyl sodium, n-propyl potassium, n-butyl lithium, as well as amides such as lithium diisopropylamide, sodium amide, lithium diethylamide, and hydrides such as sodium hydride. Typical propenyl alkylating agents include allyl bromide, allyl iodide, 2-methylallyl bromide, 2-ethylallyl p-toluenesulfonate, 2-n-propylallyl azide, 2-ethenylallyl iodide, 2-(2-propenyl)allyl azide, 2-(n-pentyl)allyl bromide and the like. The alkylation of the 4-phenyl-1,2,5,6-tetrahydropyridine is carried out by first reacting the pyridine derivative with about a 1 to 20 molar excess of a strong base in an unreactive organic solvent such as diethyl ether, tetrahydrofuran, dioxane, dichloromethane, benzene or the like. The reaction commonly is carried out at a reduced temperature of from about 10° to about −60° C. The tetrahydropyridine and the strong base are simply mixed together in a suitable solvent and stirred for about 10 to 20 minutes, and then the reaction mixture is added to a solution containing about an equimolar amount or an excess of the appropriate propenyl alkylating agent in a suitable unreactive solvent such as diethyl ether, dioxane, or the like. The alkylation reaction typically is complete within about 10 minutes to about 2 hours when carried out at a temperature of from about 25° to about −60° C. The product is readily isolated by simply adding water or brine to the reaction mixture, separating the organic layer and then removing the organic solvent, for instance by evaporation under reduced pressure. The product, a 1-alkyl-4-allyl (or 2-alkylallyl or 2-alkenylallyl)-4-phenyl-1,4,5,6-tetrahydropyridine, can be further purified if desired by conventional methods such as distillation, chromatography and the like.

The next step in the process of this invention comprises reacting the 1-alkyl-4-allyl (or 2-alkylallyl or 2-alkenylallyl)-4-phenyl-1,4,5,6-tetrahydropyridine with a protonic acid to effect cyclization and concomitant double bond migration to provide a 2-alkyl-2,3-dehydro-5-phenylmorphanium salt. Any of a number of protonic acids can be utilized to effect the cyclization and double bond migration. Commonly used acids include phosphoric acid, tetrafluoroboric acid, hydrochloric acid, sulfuric acid, nitric acid, para-toluenesulfonic acid, and related protonic acids. Phosphoric acid is a preferred protonic acid. The cyclization reaction generally is carried out in a solvent, typically an acidic solvent such as formic acid, acetic acid, sulfuric acid, hydrochloric acid or the like. Nonacidic solvents which can be used include dioxane, tetrahydrofuran and N,N-dimethylformamide. A preferred solvent is formic acid.

The allyl substituted tetrahydro pyridine typically is dissolved in an excess of protonic acid such as phosphoric acid in a suitable solvent such as formic acid. The reaction can be carried out at a temperature from about 0° C. to about 50° C., and routinely is carried out at about 20° to about 30° C. The cyclization routinely is complete within about 24 to about 72 hours. As noted in the above mechanistic scheme, the product from such protonic acid cyclization reaction is a salt, namely a 2-alkyl-2,3-dehydro-5-phenyl-7-(unsubstituted or substituted) morphanium salt. Such intermediate salt can readily be isolated by simply removing the reaction solvent and recrystallizing the salt from common solvents such as ethyl acetate, ethanol, and the like. An alternative method for obtaining the salt intermediate in a purified form comprises first making the acidic reaction mixture basic, for instance by adding a base such as sodium hydroxide, potassium hydroxide, sodium ethoxide or butyl lithium, thereby converting the 2,3-dehydrophenylmorphanium salt to a free base according to the following scheme:

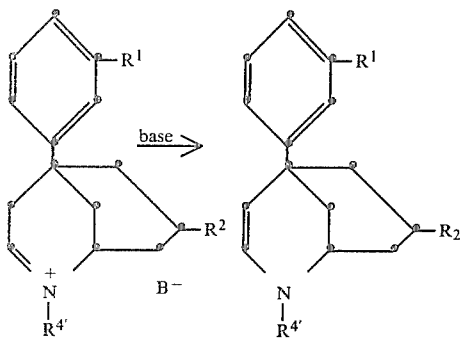

wherein $R^1$, $R^2$ and $R^{4'}$ are as defined above. The 3,4-dehydrophenylmorphan free base thus formed is readily isolated by simply extracting the alkaline reaction mixture with a water immiscible solvent such as diethyl ether or chloroform, and then removing the organic solvet by evaporation. Reaction of such free base with a protonic acid converts it back again to the corresponding 2,3-dehydrophenylmorphanium salt. Examples of typical 2-alkyl-2,3-dehydro-5-phenylmorphanium salts and 2-alkyl-3,4-dehydro-5-phenylmorphans thus prepared include the following:

2-methyl-2,3-dehydro-5-phenylmorphanium tetrafluoroborate;
2-methyl-2,3-dehydro-5-(3-methoxyphenyl)-7-methylmorphanium bromide;
2-isopropyl-2,3-dehydro-5-(3-ethoxyphenyl)-7-ethylmorphanium perchlorate;
2-cyclopropylmethyl-2,3-dehydro-5-phenyl-7-n-pentylmorphanium acetate;
2-benzyl-2,3-dehydro-5-(3-methoxyphenyl)-7-n-butylmorphanium sulfate;
2-methyl-3,4-dehydro-5-phenylmorphan;
2-ethyl-3,4-dehydro-5-(3-methoxyphenyl)-morphan;
2-isopropyl-3,4-dehydro-5-(3-ethoxyphenyl)-morphan;
2-cyclopropylmethyl-3,4-dehydro-5-(3-hydroxyphenyl)morphan;
2-benzyl-3,4-dehydro-5-phenyl-7-methyl-morphan;
2-methyl-3,4-dehydro-5-(3-methoxyphenyl)-7-ethylmorphan;
2-n-heptyl-3,4-dehydro-5-phenyl-7-n-pentylmorphan; and
2-(2-phenylethyl)-3,4-dehydro-5-(3-methoxyphenyl)-7-(3-butenyl)morphan.

The phenylmorphans of this invention which are substituted at the 3-position with an alkyl or alkenyl group are prepared by alkylation of a 2-substituted-2,3-dehydro-5-phenylmorphanium salt. Alkylating agents utilized in the reaction are defined by the formula $R^3M$ wherein $R^3$ is $C_1-C_5$ alkyl or $CH_2C_2-C_4$ alkenyl and M is a cationic radical. Commonly utilized alkylating agents include alkali metal alkyl or alkenyl metalides such as methyl lithium, ethyl sodium, n-butyl lithium, isopentyl potassium, 2-propenyl lithium, 3-butenyl sodium and related alkyl or alkenyl metalides. Additional alkylating agents which can be used are Grignard reagents of the formula $R^3$ Mg halide, such as methyl magnesium bromide and n-propyl magnesium iodide, as well as dialkyl cuprates such as diethyl cuprate and diallyl cuprate.

The alkylation reaction preferably is carried out by combining the appropriate 2-substituted-3,4-dehydro-5-phenyl-(7-substituted or unsubstituted)-morphanium salt with an equimolar amount or excess of alkylating or alkenylating agent in an unreactive organic solvent such as diethyl ether, diisopropyl ether, dioxane, tetrahydrofuran or the like. The reaction generally is complete within about two to about ten hours when carried out at about 20° to 40° C. The product, a 2,3-disubstituted-5-phenyl-(7-substituted or unsubstituted)morphan, is isolated by diluting the reaction mixture with aqueous ammonium chloride and then washing the organic layer several times with water. Separation of the organic layer and evaporation of the solvent therefrom then provides the product as a solid or an oil. Further purification can be accomplished if desired by routine methods such as column chromatography, crystallization, salt formation and the like.

The phenylmorphans of this invention which are unsubstituted at the 3-position can be prepared by reduction of a 2,3-dehydro-5-phenylmorphanium salt. For example, a salt such as 2-benzyl-2,3-dehydro-5-(3-ethoxyphenyl)-7-ethylmorphanium tetrafluoroborate can be reacted with about an equimolar quantity or excess of a reducing agent such as sodium borohydride or lithium aluminum hydride to provide the corresponding saturated phenylmorphan, i.e. 2-benzyl-5-(3-ethoxyphenyl)-7-ethylmorphan.

Such 3-unsubstituted phenylmorphans can alternatively be prepared by catalytic hydrogenation of the aforementioned 3,4-dehydro-5-phenylmorphans.

For example, a compound such as 2-cyclopropylmethyl-3,4-dehydro-5-(3-hydroxyphenyl)-7-isobutylmorphan can be hydrogenated in the presence of a suitable catalyst to provide 2-cyclopropylmethyl-5-(3-hydroxyphenyl)-7-isobutylmorphan. The catalytic hydrogenation reactions typically are carried out in organic solvents such as methanol or ethanol, and with common catalysts such as palladium on carbon, platinum, Raney nickel and the like. When the reaction is carried out at about 20° to about 50° C. with a hydrogen pressure of about 30 to about 80 psi, the reduction is substantially complete after about one-half to twenty-four hours. The reduced product is readily isolated by simply filtering the reaction mixture and then removing the reaction solvent. The phenylmorphan thus formed can be further purified if desired by routine methods such as crystallization, chromatography and salt formation.

Certain of the phenylmorphans provided by this invention are useful both as analgesics and as intermediates leading to other phenylmorphans. For example, the 2-methyl-phenylmorphans of the invention can be demethylated to provide the corresponding 2-unsubstituted phenylmorphan, which then can be alkylated with any $R^4$ alkylating agent to give the other compounds of the invention. Such demethylation is accomplished by reacting the 2-methyl-phenylmorphan with a haloformate to provide a carbamate, which is then converted to the demethylated product upon reaction with a base such as sodium or potassium hydroxide. The demethylation reaction thus contemplated is described in detail in U.S. Pat. No. 4,081,450.

The 2-benzyl-5-phenylmorphans of the invention also can be converted to 2-unsubstituted phenylmorphans which can subsequently be alkylated as desired. Debenzylation is accomplished by catalytic hydrogenation in the presence of a suitable catalyst such as platinum or palladium. For example, a phenylmorphan such as 2-benzyl-3-ethyl-5-(3-methoxyphenyl)-7-methylmorphan can be hydrogenated in the presence of palladium on carbon in ethanol for about two hours at about 50° C. under a hydrogen atmosphere of about 60 psi to effect debenzylation and thus afford 3-ethyl-5-(3-methoxyphenyl)-7-methylmorphan.

The 2-unsubstituted phenylmorphans of the invention are particularly useful as intermediates in the synthesis of other compounds of the invention. Normal alkylation with a $C_1$–$C_{10}$ alkyl, $CH_2C_2$–$C_9$ alkenyl, $C_1$–$C_3$ alkylphenyl or $CH_2C_3$–$C_6$ cycloalkyl alkylating agent affords the analgesically active phenylmorphans of this invention. For example, an alkylating agent such as allyl bromide can be reacted with a phenylmorphan such as 3-ethyl-5-phenyl-7-methylmorphan to provide 2-allyl-3-ethyl-5-phenyl-7-methylmorphan. Such alkylation reactions generally are carried out in a solvent such as dioxane or tetrahydrofuran and usually in the presence of a base such as triethylamine or pyridine to act as an acid scavenger. The reactions normally are complete after about two to four hours when carried out at about 30° to 100° C. The alkylated product is readily recovered by adding the reaction mixture to water and then extracting the aqueous mixture with a solvent such as diethyl ether, and then evaporating the organic solvent. The product thus formed can be purified by crystallization, chromatography, salt formation and the like.

The phenylmorphan compounds of this invention which have a hydroxyl substituent in the phenyl 3-position (i.e. $R^1$ is hydroxy) are preferably prepared from the corresponding 3-methoxyphenylmorphan by cleavage of the methyl ether moiety. Such cleavage generally is accomplished by reaction of a 3-methoxyphenylmorphan with acids such as hydrobromic acid and acetic acid or boron tribromide. For instance, a phenylmorphan such as 2-benzyl-3,7-diethyl-5-(3-methoxyphenyl)morphan can be dissolved in a mixture of hydrobromic acid and acetic acid and heated at reflux for about two to twenty hours. The reaction mixture next is made alkaline and the product is extracted into a solvent such as diethyl ether to provide, after removal of the solvent, the corresponding 3-hydroxyphenylmorphan derivative, namely 2-benzyl-3,7-diethyl-5-(3-hydroxyphenyl)morphan.

The phenylmorphans contemplated herein are basic in nature by virtue of the indocyclic amino group located in the 2-position. Because of such basic nature, the compounds readily form acid addition salts with any of a number of organic and inorganic acids. The pharmaceutically acceptable acid addition salts so formed are provided as an additional aspect of this invention. Such salts are those which are substantially non-toxic and can be administered to animals, including humans, for the relief of pain. The salts provided by this invention are prepared by reacting a phenylmorphan with any of a number of organic acids such as acetic acid, succinic acid, maleic acid, citric acid, p-toluenesulfonic acid, benzoic acid, as well as with any of a number of inorganic acids, including hydrochloric acid, hydrobromic acid, sulfuric acid, phosphoric acid and related acids. The pharmaceutically acceptable acid addition salts are generally highly crystalline and lend themselves to convenient purification by recrystallization from common solvents such as ethanol, water, acetone and the like.

The following listing of compounds is illustrative of the phenylmorphans provided by this invention:

2,3-dimethyl-5-(3-hydroxyphenyl)-7-ethylmorphan;
2-(2-phenylethyl)-3,7-dimethyl-5-(3-methoxyphenyl)morphan;
2-allyl-3-ethyl-5-phenylmorphan;
2-cyclobutylmethyl-3-allyl-5-(3-methoxyphenyl)-7-ethylmorphan;
2-cyclohexylmethyl-5-phenyl-7-methylmorphan;
2-(3-hexenyl)-3,7-diisopropyl-5-(3-n-propoxyphenyl)morphan;
2-(3-phenylpropyl)-3-methyl-5-(3-ethoxyphenyl)morphan;
2-n-octyl-3,7-dimethyl-5-phenylmorphan;
2-(3-ethylhexyl)-3-(2-butenyl)-5-(3-hydroxyphenyl)-7-ethylmorphan;
2-benzyl-3,7-di-n-propyl-5-(3-hydroxyphenyl)-morphan;
2-(2,3-dimethylheptyl)-3-ethyl-5-phenyl-7-methylmorphan;
2-(2-phenylethyl)-3,7-dimethyl-5-(3-hydroxyphenyl)morphan;
2-methyl-3,7-diethyl-5-phenylmorphanium bromide;
2,3,7-triethyl-5-(3-methoxyphenyl)morphanium chloride;
2-n-butyl-3-methyl-5-(3-hydroxyphenyl)morphanium acetate;
2-isopentyl-3-ethyl-5-(3-ethoxyphenyl)morphanium phosphate;
2-cyclopropylmethyl-3-methyl-5-phenyl-7-ethylmorphanium sulfate;
2-methyl-3-n-propyl-5-phenyl-7-(3-butenyl)morphanium formate;
2,7-dimethyl-3-(2-pentenyl)-5-(3-methoxyphenyl)morphanium benzoate;
2-benzyl-3,7-diethyl-5-phenylmorphanium succinate;
2-isopropyl-3,7-dimethyl-5-(3-hydroxyphenyl)morphanium p-toluenesulfonate;
2-allyl-3-(3-pentenyl)-5-(3-n-propoxyphenyl)-7-(2-butenyl)morphanium fumarate; and related compounds.

The phenylmorphan derivatives provided by this invention are useful as analgesics in the treatment of pain in animals suffering from pain and in need of treatment. The compounds have demonstrated their pain-relieving capacity in standard biological evaluations designed to measure analgesic activity. One such test is the rat-tail jerk assay. In this test, a light beam or heat source is applied to the tail of a rat. The pain threshold of the animal is measured by the latency of the rat to remove its tail from the pain source. Column 2 in the following table presents the effective subcutaneous dose in mg/kg of a number of the compounds of this invention which causes a two second delay ($ED_2$ sec) in tail removal compared to the control animals receiving no drug.

In another test designed to show analgesic activity, mice are given an intraperitaneal injection of acetic acid which causes the animals to writh. An effective analgesic is one that reduces the writhings. Column 3 of the following table presents the effective sucutaneous and oral doses in mg/kg of a compound of this invention required to reduce the writing in test animals by fifty percent ($ED_{50}$).

TABLE I

| Column I<br>Compound administered | Column II<br>Rat tail jerk<br>subcutaneous<br>injection<br>mg./kg<br>$ED_2$ seconds | Column III<br>Mouse<br>writhing | |
|---|---|---|---|
| | | s.c.<br>mg/kg<br>$ED_{50}$ | oral<br>mg/kg<br>$ED_{50}$ |
| 2-methyl-5-(3-methoxyphenyl)-morphan | 10.0 | 9.6 | 27.5 |
| 2-methyl-5-(3-hydroxyphenyl)-morphan | 1.0 | 1.3 | 29.0 |
| 2,7-dimethyl-5-(3-methoxyphenyl)morphan | 10.0 | 3.5 | 28.5 |
| 2,7-dimethyl-5-(3-hydroxyphenyl)morphan | 0.5 | 0.72 | 28.5 |
| 2,3-dimethyl-5-(3-methoxyphenyl)morphan | 15.0 | 13.0 | 17.0 |
| 2,3-dimethyl-5-(3-hydroxyphenyl)morphan | 2.0 | 2.0 | 23.0 |
| 2,3,7-trimethyl-5-(3-methoxyphenyl)morphan | 20.0 | 7.8 | 22.0 |
| 2,3,7-trimethyl-5-(3-hydroxyphenyl)morphan | 0.5 | 0.66 | 14.0 |

The phenylmorphans of this invention can be administered to humans suffering from pain and in need of relief. The compounds are effective as analgesics when administered orally or parenterally. The invention accordingly provides an analgesic method which comprises administering to a subject suffering from pain and in need of treatment an analgesically effective dose of a phenylmorphan defined by the above general formula. The compounds preferably are administered orally in the form of pharmaceutically acceptable acid addition salts. The dosage required to effect analgesia will vary somewhat depending upon the route of administration, the severity of the pain to be alleviated, as well as the particular analgesic agent selected to be administered. A typical oral dose will range from about 0.5 to about 25 mg/kg. The compounds can also be administered parenterally via the intramuscular, intravenous or subcutaneous routes. Typical parenteral doses will range from about 0.1 mg/kg to about 20 mg/kg. In severe cases of pain, the phenylmorphan may be administered via the intramuscular or intravenous routes, while maintenance therapy may be conveniently accomplished by oral dosing.

A further embodiment of this invention are pharmaceutical formulations comprising an analgesicially effective amount of a phenylmorphan having the above general formula in combinaion with any of a number of suitable diluents, excipients, carriers and the like. The formulations generally will contain from about 5 to about 50 percent by weight of active ingredient. Commonly used diluents and carriers include lactose, sucrose, starch powder, talc, magnesium stearate, magnesium oxide, calcium sulfate, acacia powder, gelatin, sodium alginate, sodium benzoate, stearic acid, and related adjuvants routinely used in formulation of pharmaceuticals. The phenylmorphans of this invention can be formulated as tablets, capsules, buccal seals, lozenges, and the like for oral administration. The compounds are conveniently formulated in aqueous saline or dextrose to constitute an injectable liquid solution for parenteral administration via the intravenous or intramuscular routes. Alternatively, the phenylmorphans can be dissolved in a suitable solvent such as water or ethanol and placed in a vial and lyophilized to provide a dry powder that is ready for reconstitution by the addition of a suitable amount of water, saline or the like. If desired, the formulations of this invention can contain additional analgesic agents such as propoxyphene hydrochloride or the like.

The following detailed examples are provided to illustrate various specific aspects of the invention.

EXAMPLE 1

1-Methyl-4-allyl-4-(3-methoxyphenyl)-1,4,5,6-tetrahydropyridine.

A solution of 74 ml. of 1.6 M n-butyl lithium was added dropwise to a cold (0° C.) stirred solution of 24.36 g. of 1-methyl-4-(3-methoxyphenyl)-1,2,5,6-tetrahydropyridine in 300 ml. of tetrahydrofuran. The reaction mixture was stirred for 10 minutes at 0° C. and then added dropwise over thirty minutes to a stirred cold (−50° C.) solution of allyl bromide in 250 ml. of diethyl ether. The reaction mixture was warmed to 0° C. and then diluted with 500 ml. of aqueous sodium chloride solution. The organic layer was separated, diluted with an additional 2 liters of diethyl ether, washed with water and dried. Removal of the solvent by evaporation under reduced pressure provided 33 g. of the crude product as an oil. The oil was distilled twice to provide 17.91 g. of 1-methyl-4-allyl-4-(3-methoxyphenyl)-1,4,5,6-tetrahydropyridine. B.P. 120°–123° C. at 0.1 torr.

Analysis calc. for $C_{16}H_{21}NO$:
Theory: C, 78.97; H, 8.70; N, 5.76.
Found: C, 78.72; H, 8.55; N, 5.48.

EXAMPLE 2

2-Methyl-3,4-dehydro-5-(3-methoxyphenyl)morphan

A solution of 1.0 g. of 1-methyl-4-allyl-4-(3-methoxyphenyl)-1,4,5,6-tetrahydropyridine dissolved in 2.5 ml. of 85.8 percent aqueous phosphoric acid and 2.5 ml. of formic acid was stirred for sixty-six hours at 24° C. under a nitrogen atmosphere. The reaction mixture then was diluted with 150 ml. of ice water and made alkaline by the addition of 50 percent aqueous sodium hydroxide. The product was extracted from the alkaline solution into diethyl ether. The ethereal extracts were combined, washed with water and dried. Removal of the solvent by evaporation under reduced pressure afforded 950 mg. of 2-methyl-3,4-dehydro-5-(3-methoxyphenyl)morphan.

Mass spec. Theory 243, Found 243.

EXAMPLE 3

2-Methyl-5-(3-methoxyphenyl)morphan

A solution of 4.0 g. of 2-methyl-3,4-dehydro-5-(3-methoxyphenyl)morphan in 150 ml. of ethanol containing 1.5 g. of five percent palladium on carbon was stirred for eighteen hours at 24° C. under a hydrogen pressure of 60 psi. The reaction mixture then was filtered and the solvent was evaporated from the filtrate to provide 3.72 g. of 2-methyl-5-(3-methoxyphenyl)morphan.

The product thus obtained was dissolved in 60 ml. of isopropanol and the solution was saturated with hydrogen bromide to form 3.22 g. of a white precipitate. The precipitated salt was recrystallized from 20 ml. of diisopropyl ether and 40 ml. of isopropanol to provide 1.0 g. of 2-methyl-5-(3-methoxyphenyl)-morphanium bromide. M.P. 152.5°–154° C.

Analysis calc. for $C_{16}H_{24}BrNO$:
Theory: C, 58.90; H, 7.41; N, 4.29.
Found: C, 59.19; H, 7.13; N, 4.04.

EXAMPLE 4

2-Methyl-5-(3-hydroxyphenyl)morphan

A solution of 2.22 g. of 2-methyl-5-(3-methoxyphenyl)morphanium bromide dissolved in a mixture of 30 ml. glacial acetic acid and 30 ml. of 48 percent aqueous hydrobromic acid was heated at reflux for sixteen hours. The reaction mixture then was cooled to room temperature, diluted with 100 ml. of water and made alkaline to pH 9.5 with sodium hydroxide solution. The alkaline solution was extracted with diethyl ether, and the ethereal extracts were combined, washed with water and dried. Removal of the solvent by evaporation under reduced pressure provided 1.29 g. of the product as a syrup. The syrup was dissolved in 25 ml. of diisopropyl ether and 125 ml. of isopropanol, and the solution was saturated with hydrogen bromide. The precipitate which formed was collected by filtration and dried to afford 1.0 g. of 2-methyl-5-(3-hydroxyphenyl)morphanium bromide. M.P. 207°–208.5° C.

Analysis calc. for $C_{15}H_{22}BrNO$:
Theory: C, 57.70; H, 7.10; N, 4.49.
Found: C, 57.45; H, 6.87; N, 4.25.

EXAMPLE 5

1-Methyl-4-(3-methoxyphenyl)-4-(2-methylallyl)-1,4,5,6-tetrahydropyridine

A solution of 74 ml. of 1.6 molar n-butyl lithium in tetrahydrofuran was added dropwise to a cold stirred solution of 24.36 g. of 1-methyl-4-(3-methoxyphenyl)-1,2,5,6-tetrahydropyridine in 300 ml. of tetrahydrofuran. After the addition was complete and the reaction mixture had been stirred at 0° C. for ten minutes, the mixture was added dropwise over thirty minutes to a stirred cold (−50° C.) solution of 10.86 g. of 3-chloro-2-methylpropene (methallyl chloride) in 250 ml. of diethyl ether. The reaction mixture was stirred and allowed to warm slowly to 0° C., at which time the reaction mixture was diluted by the dropwise addition of 500 ml. of saturated aqueous sodium chloride solution. The organic layer next was separated, diluted with 2 liters of fresh diethyl ether, washed with fresh water and dried. Removal of the solvent by evaporation under reduced pressure then provided 33.43 g. of an oil, which after distillation gave 20.97 g. of 1-methyl-4-(3-methoxyphenyl)-4-(2-methylallyl)-1,4,5,6-tetrahydropyridine. B.P. 138°–141° C. at 0.1 torr. Mass spec. Theory: 257; Found $M^+$ 257.

EXAMPLE 6

2,7-Dimethyl-2,3-dehydro-5-(3-methoxyphenyl)morphanium perchlorate

Twenty grams of 1-methyl-4-(3-methoxyphenyl)-4-(2-methylallyl)-1,4,5,6,-tetrahydropyridine were dissolved in 50 ml. of 85.8% aqueous phosphoric acid containing 50 ml. of formic acid. The reaction mixture was stirred for forty-eight hours at ambient temperature, and then diluted by the addition of 300 ml. of ice water. Fifty percent aqueous sodium hydroxide was added to the aqueous reaction mixture to pH 11, and then the product was extracted therefrom into diethyl ether. The ethereal extracts were combined, washed with water and dried. Removal of the solvent by evaporation under reduced pressure afforded 21 g. of crude oil, which after distillation gave 17.68 g. of 2,7-dimethyl-3,4-dehydro-5-(3-methoxyphenyl)morphan. B.P. 130°–138° C. at 0.1 torr.

Excess perchloric acid was added to a solution of 12.68 g. of the compound thus prepared dissolved in diethyl ether. The precipitated salt which formed was collected and recrystallized from 200 ml. of ethanol to afford 12.82 g. of 2,7-dimethyl-2,3-dehydro-5-(3-methoxyphenyl)morphanium perchlorate. M.P. 131°–133° C.

EXAMPLE 7

2,7-Dimethyl-5-(3-methoxyphenyl)morphan

A solution containing 5 g. of 2,7-dimethyl-3,4-dehydro-5-(3-methoxyphenyl)morphan dissolved in 200 ml. of ethanol containing 5 g. of five percent palladium on carbon was stirred for twenty-four hours at about 24° C. under hydrogen at 60 psi. The reaction mixture then was filtered and the solvent was removed from the filtrate by evaporation to give 4.8 g. of an oil. The oil was then dissolved in 100 ml. of diethyl ether and the solution was saturated with hydrogen bromide to effect salt formation. The salt precipitated out of solution and was collected and recrystallized from 30 ml. of diisopropyl ether and 25 ml. of isopropanol to provide 1.78 g. of 2,7-dimethyl-5-(3-methoxyphenyl)morphanium bromide. M.P. 178°–181° C.

Analysis calc. for $C_{17}H_{26}BrNO$:
Theory: C, 60.00; H, 7.70; N, 4.12.
Found: C, 59.74; H, 7.47; N, 4.38.

EXAMPLE 8

2,7-Dimethyl-5-(3-hydroxyphenyl)morphan

Following the procedure set forth in Example 4, 1.1 g. of 2,7-dimethyl-5-(3-methoxyphenyl)morphan was dissolved in a solution of 15 ml. of 48 percent hydrobromic acid and 15 ml. of glacial acetic acid, and the reaction mixture was heated at reflux for sixteen hours. Normal workup of the reaction mixture afforded 710 mg. of the product as an oil, which then was converted to its hydrobromide salt. Recrystallization of the salt from 30 ml. of diisopropyl ether and 20 ml. of isopropanol afforded 620 mg. of 2,7-dihydroxy-5-(3-hydroxyphenyl)morphanium bromide. M.P. 239°–241.5° C.

Analysis calc. for $C_{16}H_{24}BrNO$:
Theory: C, 58.90; H, 7.41; N, 4.29.
Found: C, 59.11; H, 7.30; N, 4.50.

EXAMPLE 9

2,3,7-Trimethyl-5-(3-methoxyphenyl)morphan

To a stirred solution of 60 ml. of 1.6 molar methyl lithium in diethyl ether at 24° C. was added portionwise over thirty minutes 6.0 g. of 2,7-dimethyl-2,3-dehydro-5-(3-methoxyphenyl)morphanium perchlorate (from Example 6). The reaction mixture was stirred at 24° C. for two hours following complete addition of the salt. The reaction mixture next was diluted by the addition of 30 ml. of saturated aqueous ammonium chloride, and the organic layer then was separated, washed with water and dried. Removal of the solvent by evaporation under reduced pressure afforded 4.79 g. of the product as an oil. The oil was converted to the hydrobromide salt by reaction with hydrogen bromide in diethyl ether. The salt thus formed was recrystallized from 100 ml. of diisopropyl ether and 250 ml. of isopropanol to give

15

3.18 g. of 2,3,7-trimethyl-5-(3-methoxyphenyl)morphanium bromide. M.P. 191°–194° C.

Analysis calc. for $C_{18}H_{28}BrNO$:
Theory: C, 61.02; H, 7.97; N, 3.95.
Found: C, 61.01; H, 7.79; N, 4.20.

EXAMPLE 10

2,3,7-Trimethyl-5-(3-hydroxyphenyl)morphan

Two grams of 2,3,7-trimethyl-5-(3-methoxyphenyl)morphan was reacted with hydrobromic acid and acetic acid according to the procedure set out in Example 4 to provide 1.43 g. of the title compound as a solid substance. The compound was purified by crystallization from 50 ml. of ethyl acetate and 15 ml. of ethanol to give 1.17 g. of 2,3,7-trimethyl-5-(3-hydroxyphenyl)morphan. M.P. 193° C. (dec.).

Analysis calc. for $C_{17}H_{25}NO$
Theory: C, 78.72; H, 9.71; N, 5.40.
Found: C, 78.61; H, 9.54; N, 5.20.

EXAMPLE 11

2,3-Dimethyl-5-(3-methoxyphenyl)morphan

Eight grams of 2-methyl-2,3-dehydro-5-(3-methoxyphenyl)morphanium perchlorate were reacted with 75 ml. of 1.6 molar methyl lithium in diethyl ether according to the general procedure set out in Example 9 to give 6.33 g. of 2,3-dimethyl-5-(3-methoxyphenyl)morphan. B.P. 140°–143° C. at 0.1 torr.

The compound thus formed was converted to its hydrobromide salt by reaction with excess hydrogen bromide in diethyl ether. The salt which precipitated was collected and recrystallized twice from 25 ml. of diisopropyl ether and 100 ml. of isopropanol to give 2.79 g. of 2,3-dimethyl-5-(3-methoxyphenyl)morphanium bromide. M.P. 192.5°–194° C.

Analysis calc. for $C_{17}H_{24}BrNO$:
Theory: C, 60.00; H, 7.77; N, 4.12.
Found: C, 59.87; H, 7.50; N, 4.11.

EXAMPLE 12

2,3-Dimethyl-5-(3-hydroxyphenyl)morphan

Two grams of 2,3-dimethyl-5-(3-methoxyphenyl)morphanium bromide were reacted with 25 ml. of 48 percent hydrobromic acid and 25 ml. of acetic acid according to the procedure of Example 4 to give, after purification by salt formation and recrystallization, 900 mg. of 2,3-dimethyl-5-(3-hydroxyphenyl)morphanium bromide. M.P. 237°–239° C.

Analysis calc. for $C_{16}H_{24}BrNO$:
Theory: C, 58.90; H, 7.41; N, 4.29.
Found: C, 58.69; H, 7.21; N, 4.49.

EXAMPLE 13

3,7-Dimethyl-5-(3-methoxyphenyl)morphan

To a solution of 2,3,7-trimethyl-5-(3-methoxyphenyl)morphan in dichloromethane is added a solution of phenyl chloroformate in dichloromethane. The reaction mixture is stirred for several hours at ambient temperature, and then the solvent is removed by evaporation. The residue is made alkaline by the addition of sodium hydroxide, and the alkaline solution is heated for several hours. After cooling to room temperature, the alkaline reaction mixture is extracted several times with diethyl ether. The ethereal extracts are combined, washed with water and dried. Evaporation of the solvent affords 3,7-dimethyl-5-(3-methoxyphenyl)morphan.

EXAMPLE 14

2-Cyclopropylmethyl-3,7-dimethyl-5-(3-methoxyphenyl)morphan

A solution of cyclopropylmethyl bromide in tetrahydrofuran containing 3,7-dimethyl-5-(3-methoxyphenyl)morphan and triethylamine is heated for several hours. The reaction mixture is then washed with water, and the organic solvent is next removed by evaporation under reduced pressure to provide 2-cyclopropylmethyl-3,7-dimethyl-5-(3-methoxyphenyl)morphan.

EXAMPLE 15

2-Benzyl-5-phenyl-7-ethylmorphan

A solution of 1-benzyl-4-phenyl-1,2,5,6-tetrahydropyridine in tetrahydrofuran containing n-butyl lithium is added to a solution of 3-chloro-2-ethylpropene in tetrahydrofuran. The reaction is carried out according to the procedure of Example 1 to give 1-benzyl-4-phenyl-4-(2-ethylallyl)-1,4,5,6-tetrahydropyridine. The later compound is reacted with phosphoric acid and formic acid to give, after treatment with sodium hydroxide, 2-benzyl-3,4-dehydro-5-phenyl-7-ethylmorphan. Catalytic hydrogenation of the latter compound provides 2-benzyl-5-phenyl-7-ethylmorphan.

EXAMPLE 16

2-Allyl-3-isopropyl-5-phenyl-7-ethylmorphan

A solution of 2-benzyl-3,4-dehydro-5-phenyl-7-ethylmorphan in diethyl ether is added to a stirred ethereal solution of isopropyl lithium according to the method of Example 9 to give 2-benzyl-3-isopropyl-5-phenyl-7-ethylmorphan. Catalytic hydrogenation of the latter compound effects debenzylation to provide 3-isopropyl-5-phenyl-7-ethylmorphan. Allyl bromide is reacted with the latter compound to effect N-alkylation to provide 2-allyl-3-isopropyl-5-phenyl-7-ethylmorphan.

EXAMPLE 17

The following ingredients are combined and molded into tablets for convenient oral administration to a subject suffering from pain and in need of treatment.

| | |
|---|---|
| 2-cyclopropylmethyl-3,7-dimethyl-5-(3-hydroxyphenyl)morphanium chloride | 1000 mg. |
| dextrose | 3500 mg. |
| starch powder | 500 mg. |
| | 5000 mg. |

The above formulation is compressed into 25 tablets each containing 40 mg. of active ingredient. Such tablets are administered to a person needing analgesic treatment at the rate of from 1 to about 4 tablets per day.

I claim:

1. A compound of the formula

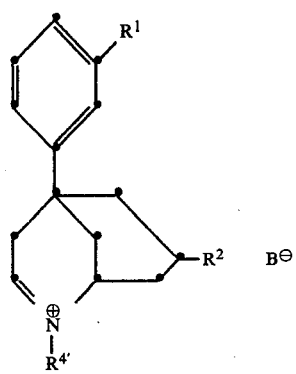 B<sup>⊖</sup> wherein:
$R^1$ is hydrogen, hydroxy or $C_1$-$C_3$ alkoxy;
$R^2$ is hydrogen, $C_1$-$C_5$ alkyl or $CH_2C_2$-$C_4$ alkenyl;
$R^{4'}$ is $C_1$-$C_{10}$ alkyl, $C_1$-$C_3$ alkylphenyl or $CH_2C_3$-$C_6$ cycloalkyl; and
$B^\theta$ is an anion of a protonic acid.

2. The compound of claim 1 wherein $R^1$ is methoxy.
3. The compound of claim 2 wherein $R^2$ is n-$C_1$-$C_5$ alkyl.
4. The compound of claim 3 wherein $R^{4'}$ is methyl or benzyl.
5. A process for preparing the compound of claim 1 comprising reacting a compound of the formula

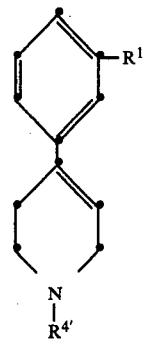

with a propenyl alkylating agent of the formula

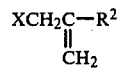

wherein:
$R^1$ is hydrogen, hydroxy or $C_1$-$C_3$ alkoxy;
$R^2$ is hydrogen, $C_1$-$C_5$ alkyl or $CH_2C_2$-$C_4$ alkenyl;
$R^{4'}$ is $C_1$-$C_{10}$ alkyl, $C_1$-$C_3$ alkylphenyl or $CH_2C_3$-$C_6$ cycloalkyl; and X is a good leaving group;
in the presence of a strong base to provide a compound of the formula

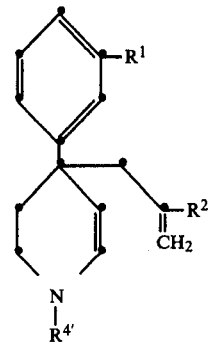

and reacting said compound with a protonic acid of the formula HB, in which B is an anion.

6. The process of claim 5 wherein $R^1$ is hydrogen or methoxy.
7. The process of claim 6 wherein $R^2$ is hydrogen.
8. The process of claim 7 wherein $R^{4'}$ is methyl.
9. The process of claim 6 wherein $R^2$ is n-$C_1$-$C_5$ alkyl.
10. The process of claim 9 wherein $R^{4'}$ is methyl or benzyl.
11. A compound of the formula

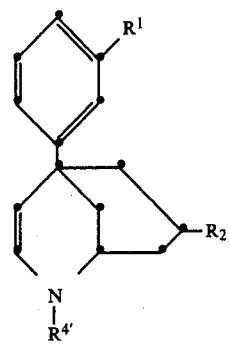

wherein:
$R^1$ is hydrogen, hydroxy or $C_1$-$C_3$ alkoxy;
$R^2$ is hydrogen, $C_1$-$C_5$ alkyl or $CH_2C_2$-$C_4$ alkenyl; and
$R^{4'}$ is $C_1$-$C_{10}$ alkyl, $C_1$-$C_3$ alkylphenyl or $CH_2C_3$-$C_6$ cycloalkyl.

12. The compound of claim 11 wherein $R^2$ is hydrogen.
13. The compound of claim 12 wherein $R^1$ is hydrogen or methoxy.
14. The compound of claim 13 wherein $R^{4'}$ is methyl or benzyl.
15. The compound of claim 11 wherein $R^2$ is n-$C_1$-$C_5$ alkyl.
16. The compound of claim 15 wherein $R^1$ is hydrogen or methoxy.
17. The compound of claim 16 wherein $R^{4'}$ is methyl or benzyl.

* * * * *